United States Patent
Grange

(10) Patent No.: US 9,134,281 B2
(45) Date of Patent: Sep. 15, 2015

(54) MOISTURE SENSOR INCLUDING, AS A MOISTURE-ABSORBING LAYER, A POLYMER LAYER INCLUDING A MIXTURE OF POLYAMIDES

(75) Inventor: Hubert Grange, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/001,917

(22) PCT Filed: Mar. 2, 2012

(86) PCT No.: PCT/EP2012/053670
§ 371 (c)(1),
(2), (4) Date: Aug. 28, 2013

(87) PCT Pub. No.: WO2012/117104
PCT Pub. Date: Sep. 7, 2012

(65) Prior Publication Data
US 2013/0336842 A1    Dec. 19, 2013

(30) Foreign Application Priority Data
Mar. 3, 2011 (FR) .................... 11 51735

(51) Int. Cl.
*G01N 30/00* (2006.01)
*G01N 27/12* (2006.01)
*B01J 20/32* (2006.01)
*G01N 27/22* (2006.01)

(52) U.S. Cl.
CPC .......... *G01N 30/00* (2013.01); *B01J 20/3204* (2013.01); *B01J 20/3272* (2013.01); *G01N 27/223* (2013.01); *B01D 2253/202* (2013.01); *B01D 2253/25* (2013.01); *B01J 2220/445* (2013.01); *G01N 27/12* (2013.01); *G01N 27/121* (2013.01); *G01N 27/126* (2013.01); *G01N 27/22* (2013.01); *G01N 2291/02845* (2013.01)

(58) Field of Classification Search
None
See application file for complete search history.

(56) References Cited

U.S. PATENT DOCUMENTS

| | | | |
|---|---|---|---|
| 3,891,958 A | | 6/1975 | Wakabayashi |
| 3,983,527 A | * | 9/1976 | Ohsato et al. ................. 338/35 |
| 4,461,808 A | * | 7/1984 | Mollison ................. 428/475.8 |
| 4,515,653 A | * | 5/1985 | Furubayashi et al. ......... 216/67 |
| 5,369,995 A | * | 12/1994 | Scheinbeim et al. ...... 73/335.02 |
| 6,342,295 B1 | * | 1/2002 | Kobayashi ................. 428/323 |
| 2004/0080325 A1 | * | 4/2004 | Ogura ........................ 324/664 |
| 2004/0087734 A1 | * | 5/2004 | Bianchi et al. .............. 525/425 |
| 2009/0200198 A1 | * | 8/2009 | Guelzow et al. ............ 206/570 |
| 2010/0173551 A1 | * | 7/2010 | Elida et al. .................. 442/414 |
| 2011/0252970 A1 | * | 10/2011 | Jones et al. .................... 95/273 |
| 2011/0293485 A1 | * | 12/2011 | Dallas et al. ................ 422/129 |

FOREIGN PATENT DOCUMENTS

| | | | | |
|---|---|---|---|---|
| JP | 60-66143 A | | 4/1985 | |
| JP | 60066143 A | * | 4/1985 | ............ G01N 27/12 |
| JP | 7-27733 A | | 1/1995 | |

* cited by examiner

*Primary Examiner* — Jennifer Wecker
(74) *Attorney, Agent, or Firm* — Hultquist, PLLC; Mary B. Grant

(57) ABSTRACT

The invention relates to a humidity sensor including, as a humidity absorbent layer, a polymer layer including a blend including a first polyamide and a second polyamide, where the said second polyamide includes, in its repetitive units, a number of carbon atoms greater than that of the repetitive units of the first polyamide.

13 Claims, 3 Drawing Sheets

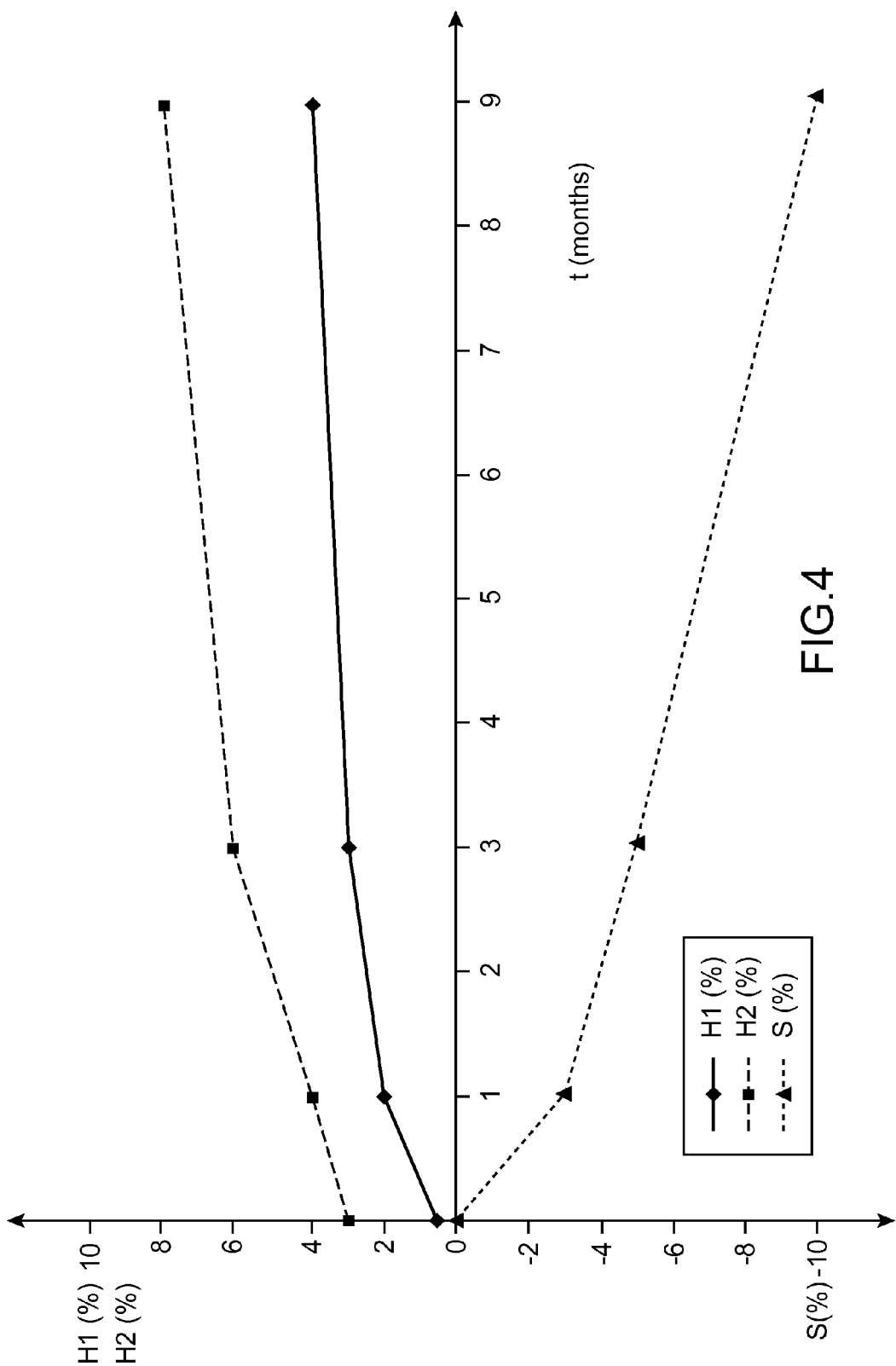

MOISTURE SENSOR INCLUDING, AS A MOISTURE-ABSORBING LAYER, A POLYMER LAYER INCLUDING A MIXTURE OF POLYAMIDES

CROSS-REFERENCE TO RELATED APPLICATIONS

This application is a U.S. national phase under the provisions of 35 U.S.C. §371 of International Patent Application No. PCT/EP12/53670 filed Mar. 2, 2012, which in turn claims priority of French Patent Application No. 1151735 filed Mar. 3, 2011. The disclosures of such international patent application and French priority patent application are hereby incorporated herein by reference in their respective entireties, for all purposes.

TECHNICAL FIELD

The present invention relates to a humidity sensor, having high water absorption rates, satisfactory sensitivity between 0 and 100% relative humidity, and also satisfactory stability of this sensitivity over time.

Humidity sensors of the invention can find applications in many fields where control of humidity is necessary, among which the following may be cited:
- the field of agriculture, where a given degree of humidity, notably in greenhouses, may be predominant for the growth of crops;
- the field of food production, where excessive humidity may increase the rate at which stocks are spoiled, and also the growth of moulds;
- the pharmaceutical field where, in particular, the moisture content of pharmaceutical products in powder form must be tightly controlled;
- the electronics field, where it is essential to be able to control the degree of humidity in clean rooms, and also to be able to detect the presence of leaks in the encapsulated electronic components;
- the chemical industry field, such as the ceramic production industry, where humidity must be controlled in connection with the drying of parts before firing, or such as the paper production industry, or again industry involving the use of gases for the synthesis of chemicals, where an excessively high moisture content in these gases may lead to a change of chemical composition of the said products;
- the field of transport and of mass consumer goods, such as motor vehicles, aviation, household electrical goods (in particular, tumble-driers);
- the medical field, for example, in controlling the humidity of expired air, or detecting leaks in a blood treatment fluid system;
- the field of conservation of works of art, where it is important to control the degree of humidity of the premises in which they are stored (for example, museum rooms) to prevent them deteriorating.

STATE OF THE PRIOR ART

Given the many abovementioned fields of application, detection and/or measurement of humidity (known by the scientific term "hygrometry") has formed the subject of many studies and analyses, which have led to the production of humidity measuring devices (also known by the term hygrometers or humidity sensors), and more specifically devices to measure relative humidity, which designates the ratio between the quantity of water vapour contained in a given medium and the maximum quantity which could be contained in it (equal to the saturation point) at a given temperature, where this ratio is expressed by a value RH which may ranges from 0 to 100%.

To be effective and reliable, hygrometers must ideally satisfy the following schedule of specifications:
- a very short response time (for example less than 2 minutes);
- a linear response as a function of relative humidity (RH) between 0 and 100%;
- a low hysteresis;
- a low temperature coefficient;
- a broad operating temperature range, preferably between −20° and 80° C.;
- stability of measurement over time (notably after the hygrometer is stored in an ambient atmosphere, with low humidity or high humidity, and/or in an aggressive medium).

Hygrometers can use a wide variety of parameters, bearing in mind the diversity of the physical phenomena in which water vapour plays a role, and each parameter leads to specific means of measurement of humidity.

Among the most commonly used hygrometers, those based on the principle of direct measurement of humidity, which is the case of condensation hygrometers, may be distinguished from those based on the principle of measurement of a property of a body relating to humidity, which is a case of variable-impedance hygrometers.

Condensation hygrometers consist, indeed, in measuring the dew point of air (i.e. the temperature at which humid air becomes saturated or, in other words, the temperature at which the water vapour it contains condenses in the form of liquid). To accomplish this a sample of the air for which it is desired to determine the relative humidity must be taken, and this must be brought, for example, into contact with a mirror which is cooled, and the temperature of which is measured. When this temperature reaches the dew point, the humidity present in the air condenses, and the light beam, which strikes the mirror, can no longer be reflected, or alternatively is reflected with a modified angle of reflection. By measuring the temperature at the instant when the beam is interrupted or modified the dew-point temperature and then the relative humidity of the air can be obtained.

In practice, this type of hygrometer has a high response time, since the temperature sensor present in the hygrometer is generally not in direct contact with the mirror, of which it must determine the temperature, which implies that a wait of several minutes is sometimes required before a limiting temperature value of the mirror is obtained.

Concerning variable-impedance hygrometers, they are based on the use of a sensitive element including a hygroscopic substance, the electrical property variations of which are measured according to the ambient humidity.

Depending on whether the electrical property the variation of which is measured is the electrical resistance or the capacity, resistive hygrometers are distinguished respectively from capacitive hygrometers.

In the case of resistive hygrometers, a deposit is made on a substrate of a quantity of hygroscopic substance in a pattern constituting a resistor. Two electrodes are connected to this pattern, and the resistance between the electrodes then depends on the water content and temperature, which enables the moisture content of the medium in which these hygrometers are positioned to be obtained, bearing in mind that the greater the quantity of water, the smaller the electrical resistance.

Finally, in the case of capacitive hygrometers, a layer of dielectric material, able to absorb the surrounding humidity, is located between two electrodes, by this means forming a condenser. When the humidity varies, the quantity of water absorbed by the said layer also varies, causing the dielectric constant of this layer to be modified, and a change of the capacity of the condenser, which is measured, and the value of the measured capacity enables the moisture content of the environment in which the capacitive hygrometer is positioned to be obtained. The dielectric materials used may be porous inorganic materials, such as porous silicon, alumina $Al_2O_3$, silica $SiO_2$, where the use of such materials leads, however, to a substantial phenomenon of hysteresis, due to the phenomenon of capillary condensation, occurring for relative humidities of between 55 and 97% RH in the case of inorganic materials conventionally having a pore diameter of between 2 and 50 nm. They may thus advantageously be used only for low-humidity measurements (for example relative humidities of less than 20% RH).

The dielectric materials used may also be organic materials, in particular polymer materials which are, conventionally, more advantageous in terms of their linearity of response and the hysteresis phenomena than in the case of inorganic materials.

These polymer materials are conventionally chosen for their ability to constitute dielectric materials with low absorption rates, such that the water vapour has greater facility for desorption when passing from a high relative humidity environment to a low relative humidity environment; materials satisfying these criteria and which are in common use belong to the family of cellulose acetate butyrates, polyimides, polysulfones or polyether sulfones.

However, these materials have certain disadvantages, among which the following may be mentioned:
low sensitivity to low humidity values (for example 0 to 5% RH) in the case of capacitive hygrometers having as a dielectric material cellulose acetatobutyrates, polyimides, polysulfones or polyether sulfones;
very long stabilisation times in the case of cellulose acetobutyrates and polyimides;
a substantial phenomenon of hysteresis in the case of relative humidities of over 8%, when the dielectric material used includes cellulose acetobutyrates or polyimides after wait times of 30 minutes for each measurement of humidity in the increasing or decreasing direction.

There is therefore a requirement for a humidity sensor (or hygrometer) with a polymer absorbent material which is able to overcome the abovementioned disadvantages and, in particular, which can have the following advantages:
stability of sensitivity over time;
high sensitivity, greater than that of the sensors involving the use of polymers such as polyimides, cellulose acetobutyrates and polyether sulfones, which will allow a measurement of very low rates of humidity (for example from 0 to 5% relative humidity) and greater measuring accuracy over the range 0 to 100% relative humidity;
very short response times;
low hysteresis.

DESCRIPTION OF THE INVENTION

The invention thus relates to a humidity sensor including, as a humidity absorbent layer, a polymer layer including a polymer blend including a first polyamide and a second polyamide, where the said second polyamide includes, in its repetitive units, a number of carbon atoms greater than that of the repetitive units of the first polyamide.

Before going into greater detail in the description of the invention, we shall specify the following definitions.

A repetitive unit is understood to mean a bivalent group derived from a component after polycondensation of it.

A polyamide is understood to mean a polycondensate including, in its main chain, amide groups —C(═O)—NH— conventionally resulting from a step of polycondensation between the amine functional groups and carboxylic acid of compounds constituting these functional groups.

Thus, by producing sensors having as a humidity absorbent layer a layer including a blend of separate polyamides (the second polyamide of which has, in its repetitive units, a carbon number higher than that of the first polyamide, in particular a group number —$CH_2$— higher than that of the first polyamide), the authors of the present invention were able to demonstrate, in a surprising manner, that the resulting sensors have a sensibility and stability over time greater than those of sensors having in their absorbent humidity layers only the said first polyamide or the said second polyamide, and notably a reduction or elimination of the phenomenon of crystallisation which might cause an irreversible deterioration of the sensitivity of the sensors.

Without being bound by theory, the stability of the sensitivity of the sensors of the invention may be explained by the stability of the proportion of the crystalline zones compared to the amorphous zones which do not crystallise under the influence of humidity, as would be the case with sensors having in their absorbent layer only a single polyamide. The rate of absorption of the sensors of the invention thus proves stable, even after temperature and humidity cycles, or after long periods in high or low humidity. In addition, the use of a blend of polyamides as defined above gives the absorbent layer a flexibility which remains stable over time, which reduces the risks of fracture experienced by the polymers or blends of polymers, which tend to crystallise and thus to harden over time.

More specifically, the polymer layer may consist solely of polyamides.

In accordance with the invention, the first polyamide may be chosen from among polyamide 6, polyamide 6-6 and polyamide 11, and the second polyamide may be chosen from among polyamide 6-6, polyamide 6-10 and polyamide 12, bearing in mind that, in accordance with the condition mentioned above, the first polyamide will be chosen from the abovementioned list such that, in its repetitive units, the number of carbon atoms is less than that of the second polyamide.

It is recalled that:
polyamide 6 is a polyamide conventionally obtained by polycondensation of caproic acid and hexamethylenediamine leading to a polyamide including a sequence of repetitive units having the following formula:

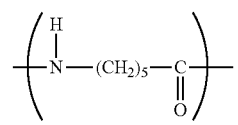

polyamide 6-6 is a polyamide conventionally obtained by polycondensation of adipic acid and hexamethylenediamine, thus leading to a polyamide including a sequence of repetitive units having the following formula:

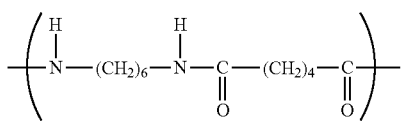

polyamide 6-10 is a polyamide conventionally obtained by polycondensation of sebacic acid and hexamethylenediamine, thus leading to a polyamide including a sequence of repetitive units having the following formula:

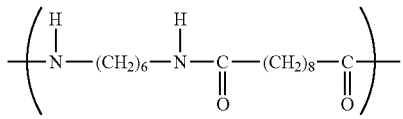

polyamide 11 is a polyamide conventionally obtained by polycondensation of aminoundecanoic acid, thus leading to a polyamide including a sequence of repetitive units having the following formula:

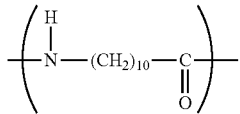

polyamide 12 is a polyamide conventionally obtained by polycondensation of aminododecanoic acid, thus leading to a polyamide including a sequence of repetitive units having the following formula:

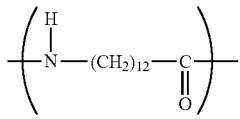

More specifically, the polymer layer may include a blend chosen from among the following blends:
a blend of polyamide 6 and polyamide 6-6;
a blend of polyamide 6 and polyamide 6-10;
a blend of polyamide 6-6 and polyamide 6-10;
a blend of polyamide 11 and polyamide 12, and preferably,
a blend of polyamide 6 and polyamide 6-6 (for example, in a 50/50 proportion by mass).

In the blends which may be used in the context of the invention, the mass proportion of the first polyamide relative to the second polyamide may range from 95/5 to 5/95, for example may be 50/50.

In addition to the presence of a first polyamide and of a second polyamide, the polymer layer may include other polyamides, such as a third polyamide, a fourth polyamide and/or a fifth polyamide.

The sensors of the invention may be capacitive or resistive sensors, in which case it may include at least one polymer layer as defined above, positioned between a first electrode and a second electrode, which first electrode and second electrode may be in contact with the same substrate.

The said support may be made of glass or of a semiconductor material, such as silicon, possibly covered with an electrical insulator layer, for example made of silicon dioxide $SiO_2$, so as to reduce the leakage currents.

The first electrode deposited on the said possible support may be made of an electrically conductive material, such as a metal material such as tantalum.

The second electrode, for its part, is also advantageously an electrically conductive material, such as a metal material and, in addition, advantageously has a porosity such that it enables the surrounding humidity to traverse the said second electrode, and to come into contact with the polymer layer. The electrically conductive material may take the form of a superposition of metal layers, such as a chromium layer, a nickel layer and a gold layer.

With such sensors the humidity may be detected by measuring the variation of the sensor's capacity or resistance.

Indeed, the humidity in contact with the polymer layer will cause a modification of its dielectric constant, causing a variation of the sensor's capacity, to which it is possible to link a relative humidity value, which is equal to that of the environment in which the said sensor is positioned.

The sensors of the invention may also take the form of a sensor including a beam or membrane covered, wholly or partly, by a polymer layer as defined above.

With such sensors detection of the humidity may be accomplished:
by measuring the variation of resonance frequency of the said powder or membrane, where the said variation depends on the absorbed mass of humidity, in which case the sensor may be considered as a sensor of the cMUT (Capacitive Micromachined Ultrasonic Transducers) type;
by measuring the surface wave caused by the absorption of humidity by the said polymer layer; or
by measuring the deformation of the said powder or membrane, caused by the absorption of humidity by the said polymer layer, which absorption causes a plasticisation of the material of the said layer, leading to a modification of the curve of the said beam or membrane, which may be detected, for example, by a piezoresistive, capacitive or optical method.

The sensors of the invention will find applications in all fields where it is required to detect the presence of humidity, or to know the quantity of humidity present in an environment, which is the case of the field of agriculture, the food production field, the pharmaceutical field, the electronics field, the chemical industry field, the transport and common consumer goods field, the medical field, and the field of conservation of works of art.

More specifically, concerning the field of electronics, the sensors of the invention may be used with a view to detecting leakages in components encapsulated in a vacuum or in nitrogen, such as sensors of the accelerometer, gyroscope or pressure type, where these sensors are conventionally protected by a cover generally made of silicon sealed with a resin bead, a fusible glass bead or a bead made of eutectic alloy or an integrated cover made of polysilicon. In the case of this type of component the sensors of the invention will enable leakages to be detected from the first ppm, since the humidity contained in the ambient atmosphere of a climate-controlled components installation room (conventionally 20 to 40% of relative humidity) will diffuse in the humidity absorbent layer of the sensors as soon as a leak appears.

The invention will now be described relative to the embodiments described above, which were supplied on an illustrative and non-restrictive basis.

BRIEF DESCRIPTION OF THE ILLUSTRATIONS

FIG. 4 is a graph illustrating the change of the hysteresis variation (respectively curves H1 and H2) (in the positive ordinate) as a function of time t (in months) and the change of sensitivity S (as a %) (curve called S) (in the negative ordinate) as a function of time t (in months) for sensors made from polyamide 6 or from polyamide 6-6 having been subjected to specific cyclings as explained below.

DETAILED DESCRIPTION OF PARTICULAR EMBODIMENTS

Example Embodiment of a Humidity Sensor in Accordance with the Invention

Figure 1:
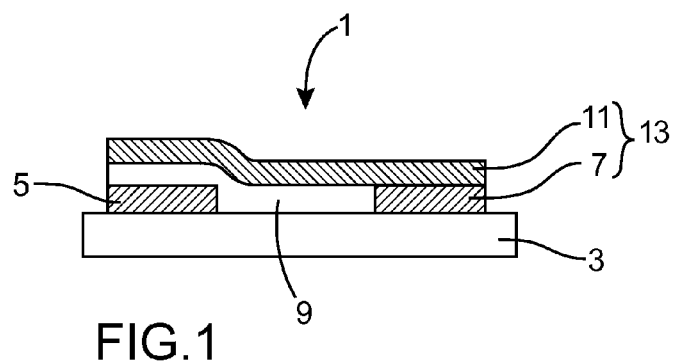
FIG. 1 represents a humidity sensor of the capacitive type in accordance with the invention.

A blend of polyamides was prepared from 1 g of polyamide 6 and 1 g of polyamide 6-6, dissolved in 40 cm$^3$ of formic acid. The blend is then deposited by spin coating at 3,000 rotations/min. on the anodised tantalum electrode belonging to a humidity sensor in accordance with the invention 1 represented in appended FIG. 1, where this sensor includes respectively:
- a glass substrate 3 having the following dimensions: 50 mm*50 mm;
- with the said anodised tantalum electrode 5 (called the first electrode) deposited through a first stencil on one face of the said substrate, where the said electrode is 250 nm thick;
- a contact electrode 7 including the superposition of a chromium layer (20 nm thick), a nickel layer (200 nm thick) and a gold layer (100 nm thick), also deposited on the said substrate through a second stencil.

The blend layer deposited in this manner (numbered 9 in FIG. 1) is subject to a heat treatment on a hot plate at 80° C. for 2 minutes, so as to eliminate the organic solvent, followed by vacuum annealing at 250° C. for 1 hour, with rapid cooling in nitrogen.

A porous chromium layer (numbered 11 in FIG. 1) 20 nm thick was then deposited, through a third stencil, by vacuum evaporation at a speed of 1 nm/second after mechanical etching of the polymer layer in contact electrode 7, where the mechanical etching was accomplished with a steel tool, so as to remove the polymer layer by scraping.

This porous chromium layer is in contact with contact electrode 7 through the holes present in the polymer layer, where the assembly formed by this layer and this contact electrode form a second electrode 13.

As a variant, it could have been envisaged to deposit a porous chromium layer simultaneously on the first electrode and the contact electrode, by means of which two vertical capacitors assembled in series would have been obtained.

The sensor obtained according to the method described above, which forms a vertical capacitor, is subjected to humidity tests.

To accomplish this the sensor is installed in an oscillator, such that the variations of capacity of the condenser may be measured when the condenser is subjected to a change of humidity.

These measurements of variation of capacity of the condenser, if the sensor is installed in an oscillator with a basic frequency of the order of 100 kHz, show that very rapid response times are obtained for a relative humidity changing from 11% to 97% RH and for a relative humidity changing from 97% to 11% RH.

Figure 2:
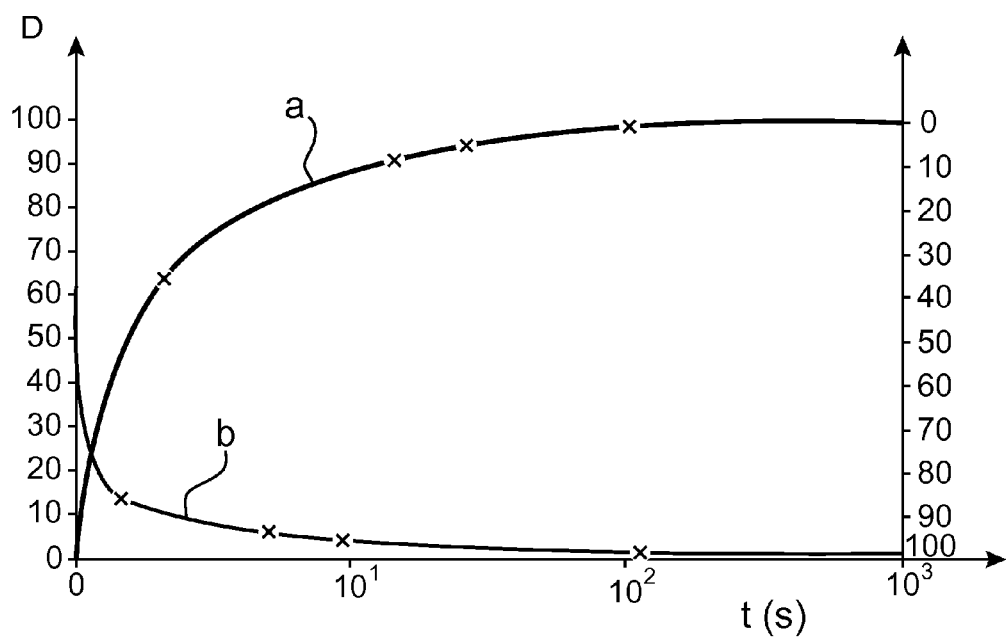
FIG. 2 is a graph illustrating the change of deviation D as a function of time t (in s) for a sensor in accordance with the invention having been subject to a change of relative humidity from 11% to 97% RH (curve a) and having been subject to a change of relative humidity from 97% to 11% RH (curve b).

Indeed, as is shown by the results reported in FIG. 2 representing the change of deviation D as a function of time t (expressed in seconds) for a change of relative humidity from 11% to 97% RH (curve a) and for a change of relative humidity from 97% to 11% RH (curve b), 98% of the deviation is obtained in less than 2 minutes in the course of the abovementioned two types of change of humidity (more specifically 1 min 43 s in respect of the change from 11% to 97% RH and 1 min 55 s in respect of the change from 97% to 11% RH).

Figure 3:
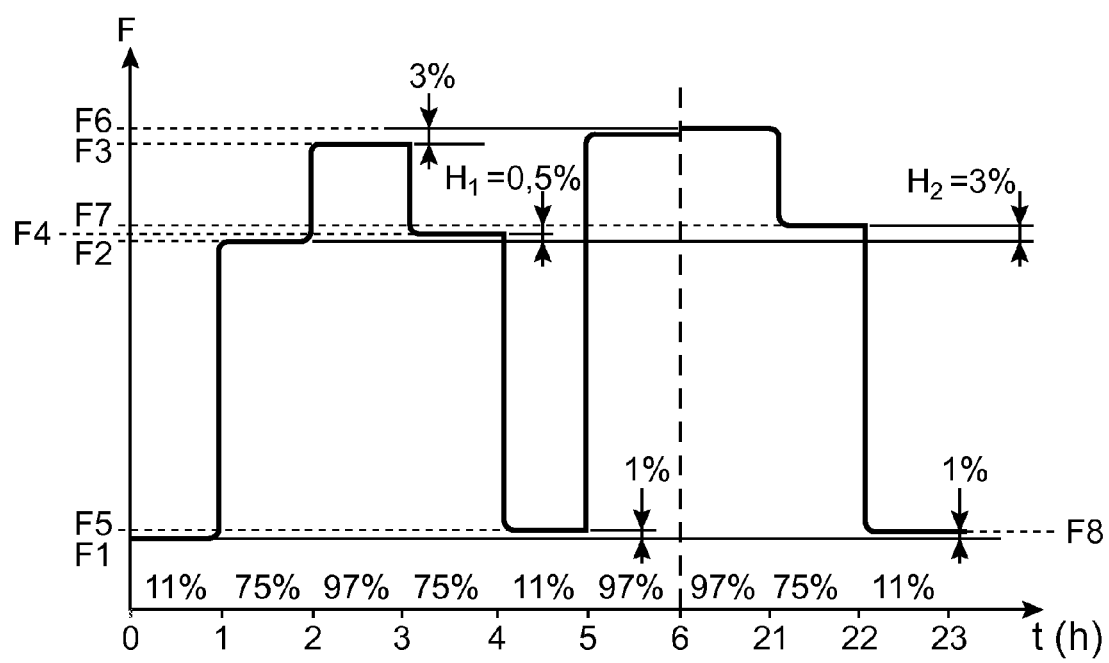
FIG. 3 is a graph illustrating the change of frequency F as a function of time t (in h) for a sensor in accordance with the invention being subject to cycling in terms of relative humidity as illustrated in this figure (where this cycling is the application of a cycle A as explained below).

The abovementioned sensor is also subject, as represented in FIG. 3, to the following cycle (called hereinafter cycle A):
- 1 hour at 11% relative humidity;
- 1 hour at 75% relative humidity;
- 1 hour at 97% relative humidity;
- 1 hour at 75% relative humidity;
- 1 hour at 11% relative humidity;
- 16 hours at 97% relative humidity;
- 1 hour at 75% relative humidity; followed by
- 1 hour at 11% relative humidity, the inverse of the capacity (i.e. the frequency) being measured in the course of this cycle.

The above cycle is used to characterise the most important parameters to be considered when humidity sensors are compared.

a) short-term hysteresis $H_1$, which is the difference between the values of frequency F obtained at 75% relative humidity before and after a period of constant conditions of 1 hour at 97% relative humidity, namely:

$$H_1 = F_4 - F_2 = 0.5\%$$

b) maximum hysteresis $H_2$, which is the difference between the value at 75% relative humidity before and after a period of constant conditions of 16 hours at 97% relative humidity:

$$H_2 = F_7 - F_2 = 3\%$$

c) sensitivity S, which is the difference between the values of frequency F obtained between the first value at 75% relative humidity and the one obtained after a period of constant conditions of 16 hours at 97% relative humidity and the first value obtained after 1 hour at 11% RH:

$$S = (F_6 - F_1)/\Delta HR \max = (F_6 - F_1)/(97-11)$$

It may be observed that the sensor in accordance with the invention has low hysteresis values in the course of this cycle.

On the subject of sensitivity, the sensors of the invention have a sensitivity 10% greater than that of sensors the sensitive element of which is made solely of polyamide 6 or polyamide 6-6.

Simultaneously, sensors in accordance with the invention identical to the abovementioned ones were subjected to cycling in accordance with abovementioned cycle A after 1 month, 3 months and 9 months of cycling in an environmental chamber according to the following cycle (also called cycle B):
- one night at 10° C. in 30% relative humidity;
- one night at 20° C. in 45% relative humidity;
- one night at 60° C. in 90% relative humidity;
- one night at 20° C. in 45% relative humidity, where the inverse of the capacity is measured in the course of the said cycle A.

After cycling in an environmental chamber, it may be observed that the sensitivity (determined on the basis of the formula given above) remains constant after 1 month, 3 months and 9 months of cycling according to cycle B.

In the case of similar sensors made of polyamide 6 or polyamide 6-6, as shown by FIG. 4, which represents in the positive ordinate the change of hysteresis (respectively H1 and H2) as a function of time (in months) and in the negative ordinate the change of sensitivity S (in %) as a function of time (in months), the sensitivity is reduced respectively by 3%, 5% and 10% after cycling of 1 month, 3 months and 9 months in an environmental chamber according to cycle B.

Concerning the hysteresis values, they increase regularly over time, namely:
- after 1 month of cycling in accordance with cycle B, H1 is equal to 2% and H2 to 4%;
- after 3 month of cycling in accordance with cycle B, H1 is equal to 3% and H2 to 6%; and
- after 9 month of cycling in accordance with cycle B, H1 is equal to 4% and H2 to 8%.

The invention claimed is:

1. A humidity sensor including, as a humidity absorbent layer, a single polymer layer consisting solely of polyamides comprising a blend including a first polyamide and a second polyamide, where the said second polyamide includes, in its repetitive units, a number of carbon atoms greater than that of the repetitive units of the first polyamide, and wherein the first polyamide is chosen from among polyamide 6, polyamide 6-6 and polyamide 11, and the second polyamide is chosen from among polyamide 6-6, polyamide 6-10 and polyamide 12.

2. A humidity sensor according to claim 1, wherein the polymer layer includes a blend chosen from among the following blends:
- a blend of polyamide 6 and polyamide 6-6;
- a blend of polyamide 6 and polyamide 6-10;
- a blend of polyamide 6-6 and polyamide 6-10;
- a blend of polyamide 11 and polyamide 12.

3. A humidity sensor according to claim 1, wherein the polymer layer includes a blend of polyamide 6 and polyamide 6-6.

4. A humidity sensor according to claim 1, wherein, in the blend, the first polyamide is present relative to the second polyamide in a mass proportion of between 95/5 and 5/95.

5. A humidity sensor according to claim 1, including at least one said polymer layer positioned between a first electrode and a second electrode.

6. A humidity sensor according to claim 5, in which the first electrode and the second electrode are in contact with a same substrate.

7. A humidity sensor according to claim 1, including a beam or a membrane covered, wholly or partly, by said polymer layer.

8. A humidity sensor according to claim 5, wherein the polymer layer includes a blend chosen from among the following blends:
- a blend of polyamide 6 and polyamide 6-6;
- a blend of polyamide 6 and polyamide 6-10;
- a blend of polyamide 6-6 and polyamide 6-10;
- a blend of polyamide 11 and polyamide 12.

9. A humidity sensor according to claim 5, wherein the polymer layer includes a blend of polyamide 6 and polyamide 6-6.

10. A humidity sensor according to claim 5, wherein, in the blend, the first polyamide is present relative to the second polyamide in a mass proportion of between 95/5 and 5/95.

11. A humidity sensor according to claim 7, wherein the polymer layer includes a blend chosen from among the following blends:
- a blend of polyamide 6 and polyamide 6-6;
- a blend of polyamide 6 and polyamide 6-10;
- a blend of polyamide 6-6 and polyamide 6-10;
- a blend of polyamide 11 and polyamide 12.

12. A humidity sensor according to claim 7, wherein the polymer layer includes a blend of polyamide 6 and polyamide 6-6.

13. A humidity sensor according to claim 7, wherein, in the blend, the first polyamide is present relative to the second polyamide in a mass proportion of between 95/5 and 5/95.

* * * * *